US006766807B2

(12) United States Patent  
Piccolo et al.

(10) Patent No.: US 6,766,807 B2
(45) Date of Patent: Jul. 27, 2004

(54) COMBINATION FLOSS DISPENSER AND TOOTHBRUSH

(76) Inventors: Snow Ellen Piccolo, 10851 King Bay Dr., Boca Raton, FL (US) 33498; Dylan Frank Piccolo, 10851 King Bay Dr., Boca Raton, FL (US) 33498

( * ) Notice: Subject to any disclaimer, the term of this patent is extended or adjusted under 35 U.S.C. 154(b) by 77 days.

(21) Appl. No.: 10/075,949

(22) Filed: Feb. 15, 2002

(65) Prior Publication Data

US 2002/0121283 A1 Sep. 5, 2002

Related U.S. Application Data

(60) Provisional application No. 60/273,203, filed on Mar. 5, 2001.

(51) Int. Cl.[7] .............................................. A45D 44/18
(52) U.S. Cl. ...................................... 132/309; 132/325
(58) Field of Search ................................ 132/309, 311, 132/321–329; 15/22.1, 22.2, 23

(56) References Cited

U.S. PATENT DOCUMENTS

| | | | |
|---|---|---|---|
| 1,773,041 A | 8/1930 | Healy | |
| 3,782,397 A | 1/1974 | McCord | |
| 3,853,134 A | * 12/1974 | McCord | ................... 132/309 |
| 3,890,986 A | 6/1975 | Gerlich | |
| 4,821,752 A | 4/1989 | Widlak | |
| 4,887,621 A | 12/1989 | Vallieres | |
| 5,137,260 A | * 8/1992 | Pehr | ............................ 215/216 |
| 5,676,167 A | 10/1997 | Garner | |
| 5,701,921 A | * 12/1997 | Father et al. | ............... 132/309 |
| 5,769,102 A | * 6/1998 | Zebuhr | ....................... 132/322 |
| 5,832,940 A | 11/1998 | Embry et al. | |
| 5,924,429 A | 7/1999 | Morando | |
| 6,360,395 B2 | * 3/2002 | Blaustein et al. | .............. 15/28 |

* cited by examiner

Primary Examiner—Kevin Shaver
Assistant Examiner—Stephanie Willatt
(74) Attorney, Agent, or Firm—Oltman, Flynn & Kubler

(57) ABSTRACT

A dental floss dispenser includes a floss spool having two spool ends and wound with a certain length of floss; a dispenser body including an external dispenser first end wall and an external dispenser second end wall and a longitudinal external dispenser side wall extending between the dispenser first and second end walls, and containing a spool retaining floss bore sized to longitudinally receive the floss spool wound with floss, the floss bore having a bore opening in the dispenser first end wall, a bore side wall and a bore end wall with a spool end recess for receiving an end of the floss spool; a floss panel covering the floss bore opening and retaining the floss spool, the floss panel having a floss panel port through which the floss may be progressively passes when dispensed; a floss cutting element; and a floss bore door hingedly mounted to the dispenser body adjacent to the bore opening, and sized and oriented to close over and cover the floss panel.

10 Claims, 4 Drawing Sheets

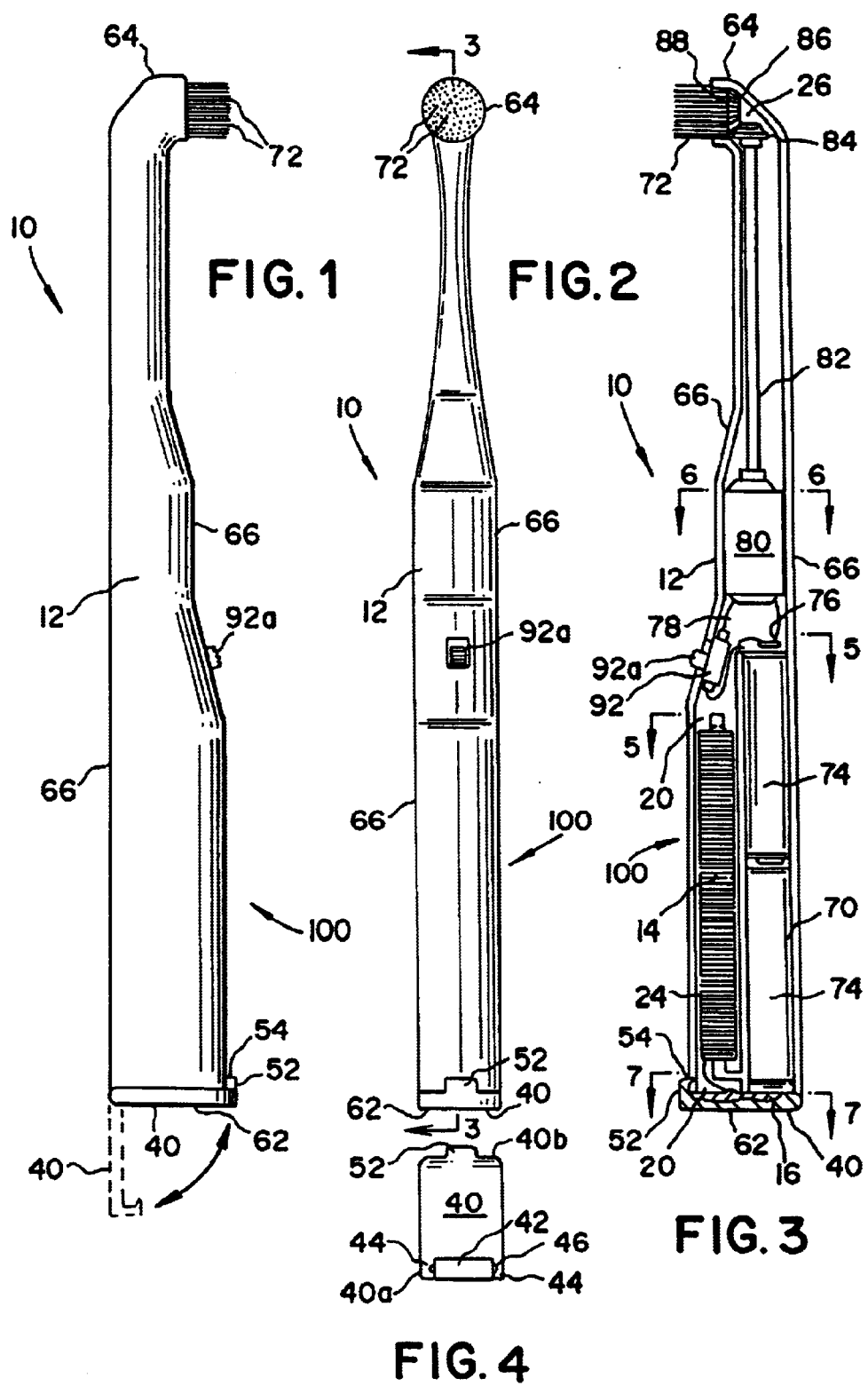

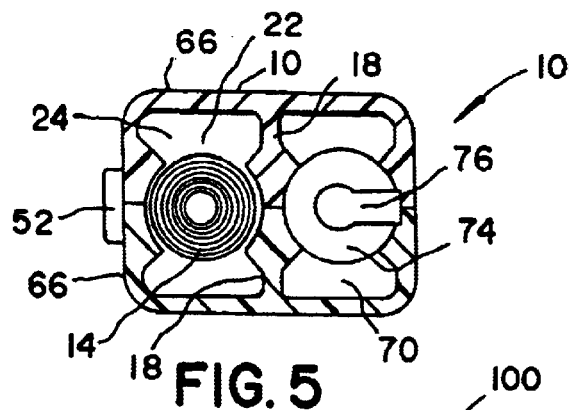
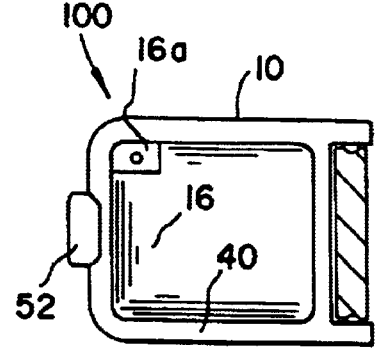
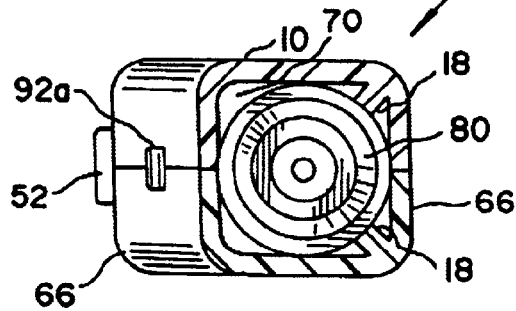
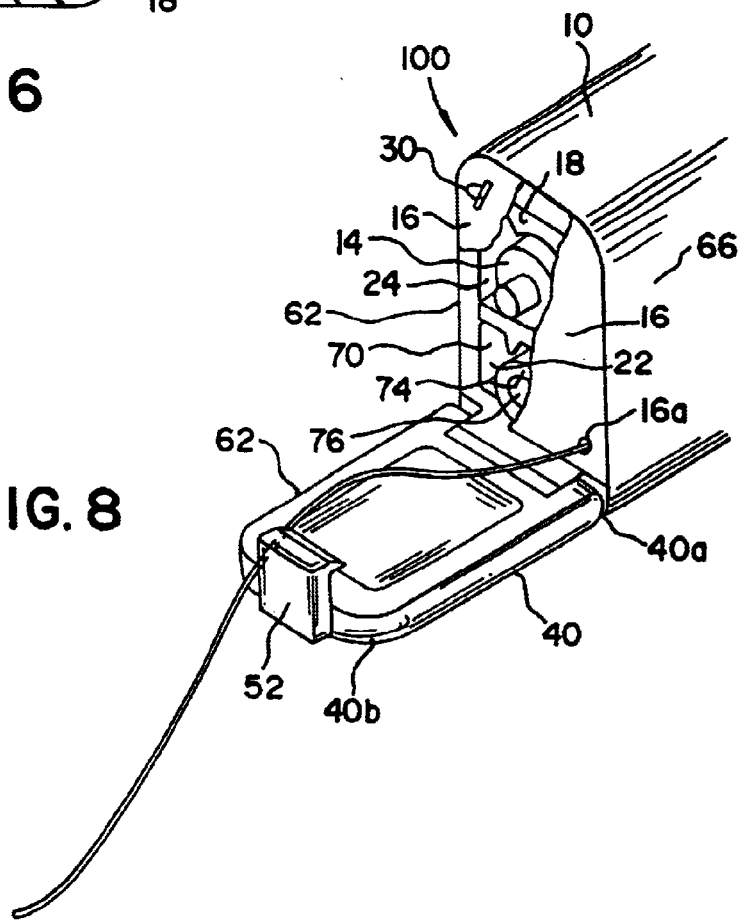
FIG. 5
FIG. 6
FIG. 7
FIG. 8

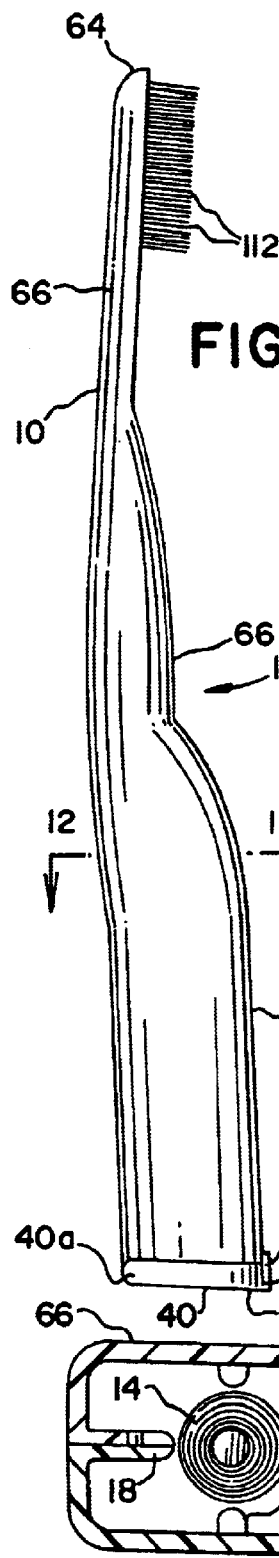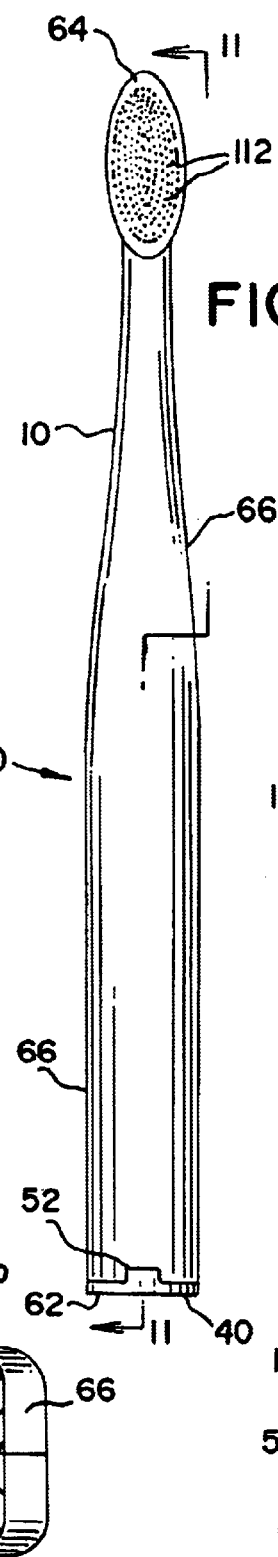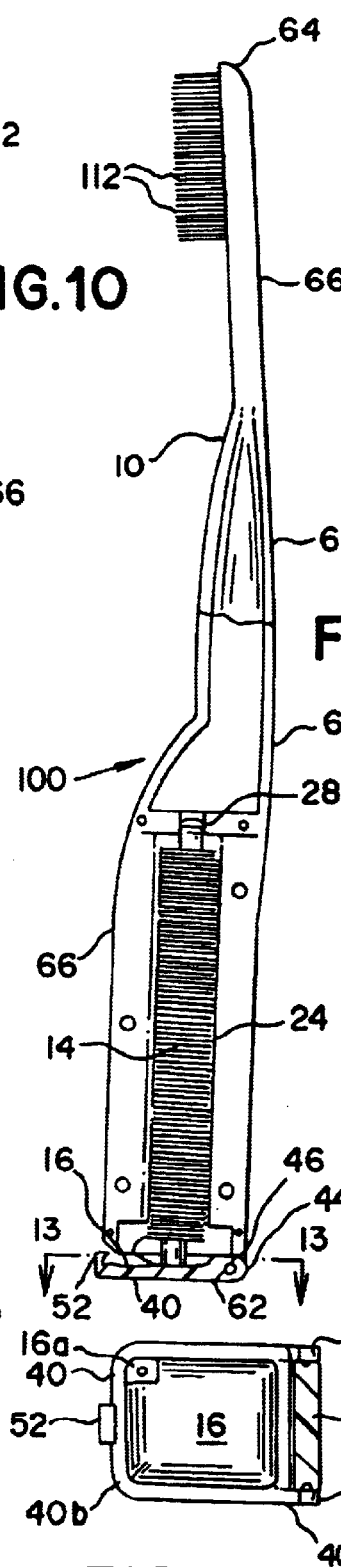

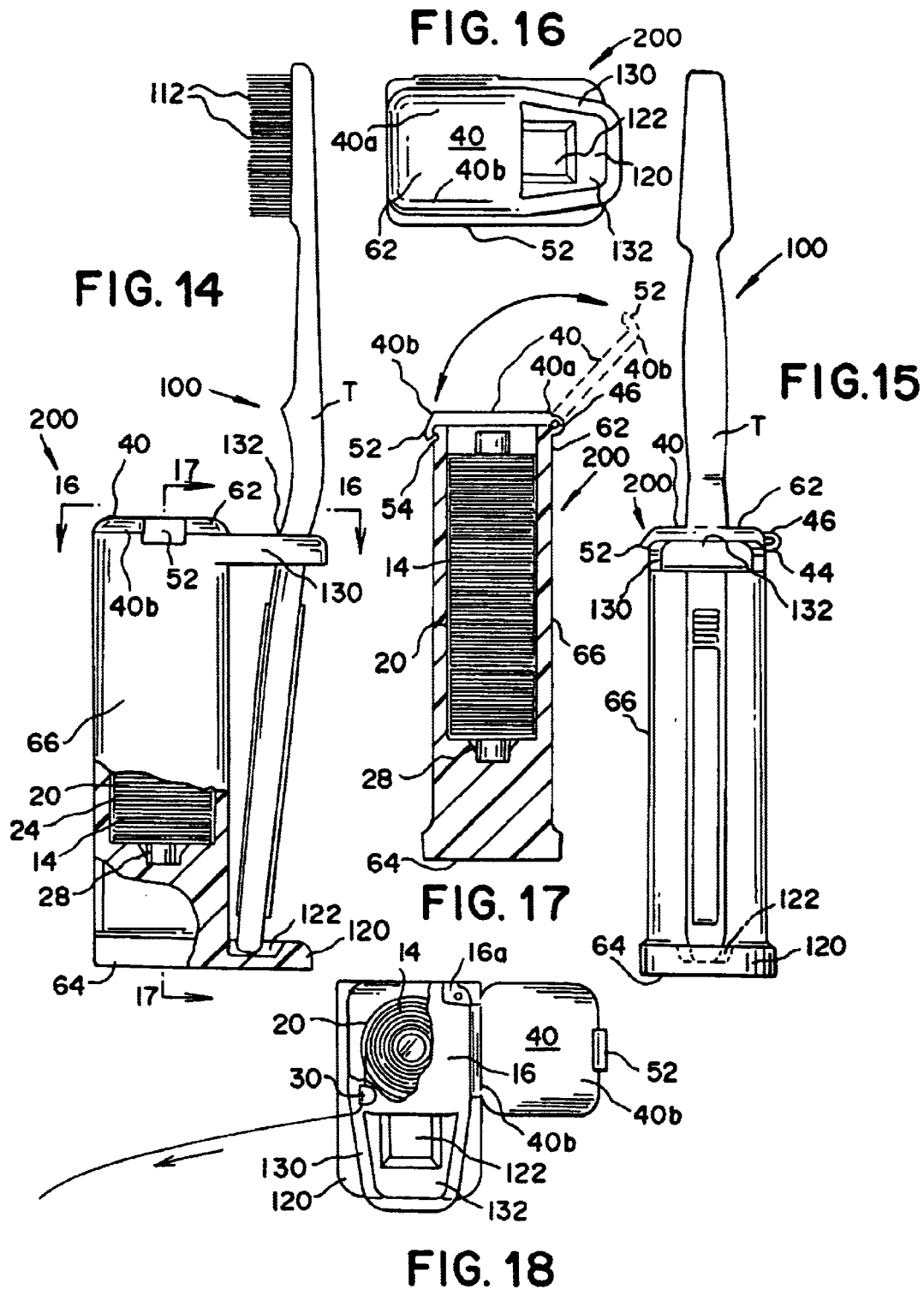

COMBINATION FLOSS DISPENSER AND TOOTHBRUSH

FILING HISTORY

This application continues from provisional application serial No. 60/273,203, filed on Mar. 5, 2001.

BACKGROUND OF THE INVENTION

1. Field of the Invention

The present invention relates generally to the field of oral hygiene and tooth cleaning devices. More specifically the present invention relates to a dental floss dispenser shaped to define a toothbrush handle or toothbrush holder, the floss dispenser including a dispenser body containing a spool retaining floss bore sized to longitudinally receive a floss spool wound with a certain length of floss, the floss bore having a bore opening, a floss panel covering the bore opening and retaining the floss spool, the floss panel having a panel port through which the floss passes when dispensed, a bore side wall and a bore end wall with a beveled spool end recess for receiving and centering an end of the floss spool, a floss cutting element secured adjacent or directly to the floss panel, and a floss bore door hingedly mounted to the dispenser body adjacent to the bore opening, and sized and oriented to close over and cover the floss panel for maintaining hygiene of floss remaining on the spool.

The dispenser body preferably is elongate and has external dispenser first and second end walls and an external longitudinal dispenser side wall extending between the dispenser first and second end walls, and the floss panel preferably extends across the dispenser first end wall.

For a first embodiment, the dispenser body narrows as it approaches the dispenser second end wall and as a whole defines the handle of a toothbrush. The dispenser second end wall is of sufficient area to permit the toothbrush to stand upright on the dispenser second end wall. The length of floss on the spool is selected to last only until the toothbrush requires replacement, so that the floss running out is a signal to the user to purchase a new toothbrush. The toothbrush includes an electrically powered cluster of movable bristles, and may additionally include a cluster of fixed bristles. A variation of the first embodiment differs primarily in that the electric drive mechanism is omitted, and only a cluster of fixed bristles is provided. For a second embodiment, the dispenser body is configured as a toothbrush holder, which may have the shape of an animal or plant figure, such as a bear or a flower. In a preferred configuration, the dispenser second end wall once again is of sufficient area to permit the dispenser to stand upright on the dispenser second end wall.

2. Description of the Prior Art

There have long been floss dispensers configured to be part of or integrated into toothbrushes. Most do not provide protection against floss contamination between uses, and none teach providing an amount of floss which becomes exhausted with normal use at the same time the bristles are sufficiently worn to require replacing.

McCord, U.S. Pat. No. 3,782,397, issued on Jan. 1, 1974, teaches a toothbrush and dental-floss dispenser. McCord teaches a dental floss dispenser contained within the toothbrush handle, including a spool wound with floss mounted inside a bore within the handle and opening out of the handle proximal end, the floss being dispensed through a floss port in a side of the handle. The handle proximal end is covered with a removable end cap.

Vallieres, U.S. Pat. No. 4,887,621, issued on Dec. 19, 1989, reveals a combination toothbrush and dental floss holder. Once again, a spool wound with dental floss is mounted inside a bore within the handle. The floss is dispensed through a floss port in the handle proximal end, which is covered with an end cap.

Garner, U.S. Pat. No. 5,676,167, issued on Oct. 14, 1997, discloses a toothbrush having a floss dispenser box at the toothbrush handle proximal end. The dispenser box has a box door which opens to expose a spool of floss and has a floss cutter mounted on the outside of the dispenser box. A problem with Garner is that the floss cutter is exposed and subject to contamination when the brush is not in use, and the floss spool is exposed during use so that moisture can enter the compartment during use and remain in the dispenser box, creating a disease breeding ground.

Healy, U.S. Pat. No. 1,773,041, issued on Aug. 12, 1930, teaches a toothbrush having a handle containing a compartment opening out of the handle proximal end into which a floss spool cartridge fits. A problem with Healy is that the segment of floss next to be used is always exposed and can become unsanitary between toothbrush uses.

Widlak, U.S. Pat. No. 4,821,752, issued on Apr. 18, 1989, reveals an oral hygiene apparatus having a replaceable tooth engaging cleaning element and an internal dental filament dispenser. A roll of dental floss is provided in a toothbrush handle proximal end and covered with an end panel with a floss release port and with a pivoting floss door having a floss cutter mounted to the door free end.

Gerlich, U.S. Pat. No. 3,890,986, issued on Jun. 24, 1975, discloses a teeth cleaning unit including a toothbrush having a tubular handle proximal end defining a floss compartment containing a floss spool. The floss compartment has an removably end cap with a floss passing opening and a cutting element affixed to the exterior of the end cap. A problem with Gerlich is that the next segment of floss to be used is always exposed and subject to health threatening contamination.

Morando, U.S. Pat. No. 5,924,429, issued on Jul. 20, 1999, teaches a disposable toothbrush system with integral dental floss supply. Morando includes a handle for removably receiving a toothbrush, the handle containing a floss compartment containing a roll of dental floss, and provision for the withdrawal of dental floss through a side port. A problem with Morando is that a moist used toothbrush apparently is placed into the floss compartment together with the floss, leading to floss contamination between toothbrush uses.

Embry, et al., U.S. Pat. No. 5,832,940, issued on Nov. 10, 1998, discloses a self-contained toothbrush construction. Embry, et al. includes a tubular toothbrush holder and a toothbrush having a hollow handle forming a reservoir for dentifrice.

It is thus an object of the present invention to provide a combination floss dispenser and toothbrush which provides protection against floss contamination between uses.

It is another object of the present invention to provide such a combination floss dispenser and toothbrush which contains an amount of floss which becomes exhausted with normal use at the same time the toothbrush bristles are sufficiently worn that replacement is recommended.

It is still another object of the present invention to provide such a combination floss dispenser and toothbrush in which a dispenser end wall is of sufficient area that the dispenser can stands upright with substantial stability on the dispenser end wall on a flat surface.

It is yet another object of the present invention to provide such a combination floss dispenser and toothbrush in which the dispenser has an attractive sculptured shape.

It is finally an object of the present invention to provide such a combination floss dispenser and toothbrush which is easy to use, attractive and inexpensive to manufacture.

SUMMARY OF THE INVENTION

The present invention accomplishes the above-stated objectives, as well as others, as may be determined by a fair reading and interpretation of the entire specification.

A dental floss dispenser is provided including a floss spool having two spool ends and wound with a certain length of floss; a dispenser body including an external dispenser first end wall and an external dispenser second end wall and a longitudinal external dispenser side wall extending between the dispenser first and second end walls, and containing a spool retaining floss bore sized to longitudinally receive the floss spool wound with floss, the floss bore having a bore opening in the dispenser first end wall, a bore side wall and a bore end wall with a spool end recess for receiving an end of the floss spool; a floss panel covering the floss bore opening and retaining the floss spool, the floss panel having a floss panel port through which the floss may be progressively passes when dispensed; a floss cutting element; and a floss bore door hingedly mounted to the dispenser body adjacent to the bore opening, and sized and oriented to close over and cover the floss panel.

The floss cutting element optionally is secured to the floss panel. The floss panel has an outward surface and the floss cutting element optionally is secured to the floss panel outward surface.

The dispenser body optionally is elongate to define a toothbrush handle, and additionally includes cleaning bristles protruding laterally from the toothbrush handle, the length of the certain length of floss being such that the certain length of floss becomes fully dispensed when the bristles are worn from use sufficiently to require replacement.

The dental floss dispenser preferably additionally includes a first hinge flange protruding longitudinally outwardly from the dispenser first end wall, the floss bore door preferably has a door hinged end and a door free end; and a second hinge flange protruding from the door hinged end and spaced apart sufficiently to receive longitudinally between them the first hinge flange, the first hinge flange and the second hinge flange including registering segments of a hinge pin passageway extending through the first and second door hinge flanges; and a hinge pin extending through the segments of the hinge pin passageway so that the door pivots on the hinge pin. The dental floss dispenser preferably additionally includes a door latch notch in the dispenser side wall and a barbed latching tab protruding from the door free end positioned to releasibly and engagingly snap into the door latch notch to releasibly hold the floss bore door closed.

The dental floss dispenser optionally additionally includes an electrically powered cluster of movable bristles. The dispenser body optionally includes a bristle opening in the dispenser side wall, and a mechanism compartment adjacent to the floss bore and extending toward the dispenser second end wall, the mechanism compartment containing a battery, a battery electrical contact electrically contacting the battery, circuit wiring electrically connected to the battery electrical contact, an electric motor electrically connected to the circuit wiring, the motor including a drive mechanism extending toward the dispenser second end wall and driving the cluster of movable bristles extending out of the bristle opening. The floss bore door in this instance is sized to cover both the floss bore and the mechanism compartment when closed, and where the floss bore door simultaneously exposes the floss bore and the mechanism compartment when opened. The dental floss dispenser preferably additionally includes an off/on switch controlling the flow of electricity from the battery to the motor. The dental floss dispenser preferably still additionally includes a cluster of fixed bristles extending from the dispenser side wall adjacent to the cluster of movable bristles.

The dispenser body optionally narrows as it approaches the dispenser second end wall, and additionally includes a fixed cluster of bristles mounted to and protruding laterally outward from the dispenser side wall adjacent to the dispenser second end wall. The floss bore optionally is wider than the floss spool wound with floss and includes several longitudinal guide ribs projecting radially inwardly to loosely abut and slidably retain the floss spool wound with floss, for providing a wider external gripping area and to be light in weight.

The dispenser body alternatively is configured as a toothbrush holder, and the second end wall has enough area that the dispenser can stand upright on the dispenser second end wall, and additionally includes a foot flange protruding laterally at the dispenser second end wall for increasing dispenser stability; and a retaining flange protruding laterally at the dispenser first end wall above the foot flange and having a toothbrush passing port. The foot flange preferably includes a foot flange recess for receiving and retaining an end of a toothbrush; so that an end of a toothbrush may be laterally retained by the foot flange recess and the toothbrush may be laterally retained by sides of the toothbrush passing port.

BRIEF DESCRIPTION OF THE DRAWINGS

Various other objects, advantages, and features of the invention will become apparent to those skilled in the art from the following discussion taken in conjunction with the following drawings, in which:

FIG. 1 is a first side view of the first embodiment of the inventive dispenser configured as a toothbrush handle containing a floss spool and an electric motor assembly driving a cluster of movable bristles.

FIG. 2 is a front view of the embodiment of FIG. 1.

FIG. 3 is a cross-sectional second side view of the embodiment of FIG. 1.

FIG. 4 is an end view of the first end wall of the embodiment of FIG. 1.

FIG. 5 is a cross-sectional view of the embodiment of FIG. 1 taken along line 5—5 of FIG. 3, showing the floss spool and a motor assembly battery.

FIG. 6 is a cross-sectional view of the embodiment of FIG. 1 taken along line 6—6 of FIG. 3.

FIG. 7 is a cross-sectional view of the embodiment of FIG. 1 taken along line 7—7 of FIG. 3.

FIG. 8 is a broken away perspective view of the first end wall of the embodiment of FIG. 1 with the floss door open to reveal the floss panel, which is shown broken away to reveal the floss spool and a battery of the motor assembly.

FIG. 9 is a first side view of the variation of the first embodiment of the inventive dispenser configured as a toothbrush handle containing a floss spool only and having a cluster of fixed bristles.

FIG. 10 is a front view of the embodiment variation of FIG. 9.

FIG. 11 is a cross-sectional second side view of the embodiment variation of FIG. 9.

FIG. 12 is a cross-sectional view of the embodiment of FIG. 9 taken along line 12—12 of FIG. 9.

FIG. 13 is a cross-sectional view of the embodiment of FIG. 9 taken along line 13—13 of FIG. 11.

FIG. 14 is a side view of the second embodiment of the dispenser shown retaining a toothbrush.

FIG. 15 is a front view of the embodiment of FIG. 14.

FIG. 16 is a top view of the embodiment of FIG. 14 showing the floss bore door in the closed position.

FIG. 17 is a cross-sectional front view of the embodiment of FIG. 14, with the floss door shown closed in solid lines and shown open in broken lines, revealing the floss spool within the floss bore.

FIG. 18 is a top view of the embodiment of FIG. 14 showing the floss bore door in the open position.

DETAILED DESCRIPTION OF THE PREFERRED EMBODIMENTS

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Reference is now made to the drawings, wherein like characteristics and features of the present invention shown in the various FIGURES are designated by the same reference numerals.

The Invention Generally

Referring to FIGS. 1–18, a dental floss dispenser 10 is disclosed which is shaped to define a handle of a toothbrush 100 or a toothbrush holder 200, the floes dispenser 10 including a dispenser body 12 containing a spool retaining floss bore 20 sized to longitudinally receive a floss spool 14 wound with floss, the floss bore 20 having a bore opening 22, a floss panel 16 covering the bore opening 22 and retaining the floss spool, the floss panel 16 having a panel port 16a through which the floss passes and is dispensed, panel port 16a preferably being passed through a corner of floss panel 16, a bore side wall 24 and a bore end wall 26 with a beveled spool end recess 28 for rotatably receiving and centering an end of the floss spool 14, a floss cutting element 30 secured adjacent or directly to floss panel 16, preferably at a floss panel 16 corner diagonally across from the panel port 16a corner, and a floss bore door 40 hingedly mounted to dispenser body 12 adjacent to bore opening 22, and sized and oriented to close over and cover floss panel for maintaining hygiene of the floss remaining on the spool 14.

Dispenser body 12 preferably is elongate and has an external dispenser first end wall 62 and a dispenser second end wall 64 and an external longitudinal dispenser side wall 66 extending between dispenser first and second end walls 62 and 64, respectively, and floss panel 16 preferably extends across dispenser first end wall 62.

To mount floss bore door 40, a first hinge flange 42 preferably protrudes longitudinally outwardly from the dispenser first end wall 62 and the floss bore door 40 preferably has two second hinge flanges 44 protruding from a door hinged end 40a and spaced apart sufficiently to receive longitudinally between them the first hinge flange 42. Registering segments of a hinge pin passageway extend through the first and second door hinge flanges 42 and 44, and a hinge pin 46 fits through the segments of the hinge pin passageway such that the door 40 pivots on the hinge pin 46. A barbed latching tab 52 protrudes perpendicularly from a door free end 40b and releasibly and engagingly snaps into a door latch notch 54 to hold the door 40 closed.

First Preferred Embodiment

For a first embodiment, the dispenser body 12 narrows as it approaches the dispenser second end wall 64 and as a whole defines the handle of toothbrush 100. See FIGS. 1–8. The length of floss on the spool 14 is selected to last only until the toothbrush 100 requires replacement such as for worn bristles, so that the floss running out, is a signal to and a motivating factor for the user to purchase a new toothbrush 100. For example, twelve to eighteen feet of floss may be provided, which is recommended by the American Dental Association, as the amount used during the life of ordinary toothbrush bristles. The floss preferably is flavor coated or flavor impregnated, such as with mint, cherry or other suitable flavoring material. The first end wall 62 is of sufficient cross-sectional area to permit the dispenser to stand upright on the first end wall. The toothbrush 100 includes an electrically powered cluster of movable bristles 72. The dispenser body 12 includes a mechanism compartment 70 extending parallel to and beyond the floss bore 20 to the dispenser body second end wall 64. The mechanism compartment 70 contains replaceable batteries 74, battery electrical contacts 76 and wire circuit 78, an electric motor 80 electrically connected to the batteries 74, the motor 80 including a drive shaft 82 extending toward the dispenser second end wall 64 and terminating in a first bevel gear 84 meshing with a perpendicular second bevel gear 86 fitted with the cluster of movable bristles 72 extending out of a bristle opening 88 in the dispenser side wall 66. The floss bore door 40 preferably is sized to cover both the floss panel 16 and the mechanism compartment 70 when closed, and opens to simultaneously expose the floss panel 16 and the mechanism compartment 70. Where the batteries 74 are not replaceable, the floss panel 16 extends over the mechanism compartment as well. The circuit 78 contains an off/on switch 92 controlling the flow of electricity to the motor 80, and a switch actuating lever 92a protrudes from the switch 92 out of the dispenser body 12 through a switch port. It is contemplated that a cluster of fixed bristles 112 optionally extend from the dispenser side wall 66 in addition and parallel to the cluster of movable bristles 72.

In a variation of the first embodiment, the dispenser body 12 once again narrows as it approaches the dispenser second end wall 64 and as a whole defines the handle of a toothbrush 100, and has a cluster of fixed bristles 112 mounted to and protruding laterally outward from the dispenser side wall 66 adjacent to the dispenser second end wall 64. See FIGS. 9–13. For this embodiment, the floss bore 20 preferably is wider than a floss spool 14 fully wound with floss and longitudinal guide ribs 18 protrude radially inwardly to loosely abut and slidably retain a floss spool 14, to provide a wider external gripping area, to conserve dispenser body 12 material and to make the dispenser body 12 relatively light in weight.

Second Preferred Embodiment

For a second embodiment, the dispenser body 12 is configured as a toothbrush holder 200, and the dispenser body preferably has the shape of an animal or plant figure, such as of a bear or a flower. See FIGS. 14–18. In a preferred configuration, the dispenser body 12 stands upright on the dispenser second end wall 64, which has sufficient area to permit this. The floss spool 14 preferably holds more floss than in the toothbrush embodiments, perhaps 100 yards, and once again the floss preferably is coated or impregnated with flavor material. A foot flange 120 protrudes laterally from the dispenser second end wall 64 to increase dispenser stability and includes a foot flange recess 122 in the foot flange 120 upper surface for receiving and retaining an end of a conventional toothbrush T. A retaining flange 130 protrudes laterally from the dispenser side wall 66 adjacent to the dispenser first end wall 64 directly above the foot flange 120 and includes a toothbrush passing port 132, so that the lower end of the toothbrush is laterally retained by the foot flange recess 122 and the toothbrush T upper end is laterally retained by the sides of the toothbrush passing port 132.

While the invention has been described, disclosed, illustrated and shown in various terms or certain embodiments or modifications which it has assumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. A dental floss dispenser, comprising:

a floss spool having two spool ends and wound with a certain length of floss;

and an electrically powered cluster of movable bristles;

a dispenser body including an external dispenser first end wall and an external dispenser second end wall and a longitudinal external dispenser side wall extending between said dispenser first and second end walls, and containing a spool retaining floss bore sized to longitudinally receive said floss spool wound with floss, said floss bore having a bore opening in said dispenser first end wall with a, a bore side wall and a bore end wall with a spool end recess for receiving an end of said floss spool, said dispenser body further including a bristle opening in said dispenser side wall, and a mechanism compartment adjacent to said floss bore and extending toward said dispenser second end wall, said bore side wall separating said mechanism compartment and said floss bore and said mechanism compartment containing a battery, a battery electrical contact electrically contacting said battery, circuit wiring electrically connected to said battery electrical contact, an electric motor electrically connected to said circuit wiring, said motor including a drive means extending toward said dispenser second end wall and driving said cluster of movable bristles extending out of said bristle opening;

a floss panel covering said floss bore opening and retaining said floss spool, said floss panel having a floss panel port through which said floss may be progressively passed when dispensed;

a floss cutting element;

and a floss bore door hingedly mounted to said dispenser body adjacent to said bore opening, and sized and oriented to close over and cover both said floss bore and said mechanism compartment when closed, and wherein said floss bore door simultaneously exposes said floss bore and said mechanism compartment when opened.

2. The dental floss dispenser of claim 1, wherein said floss cutting element is secured to said floss panel.

3. The dental floss dispenser of claim 1, wherein said floss panel has an outward surface and wherein said floss cutting element is secured to the floss panel outward surface.

4. The dental floss dispenser of claim 1, wherein said dispenser body is elongate to define a toothbrush handle, the length of said certain length of floss being such that said certain length of floss becomes fully dispensed when said bristles are worn from use sufficiently to require replacement.

5. The dental floss dispenser of claim 4, wherein said dispenser body narrows as it approaches said dispenser second end wall, additionally comprising a fixed cluster of bristles mounted to and protruding laterally outward from said dispenser side wall adjacent to said dispenser second end wall.

6. The dental floss dispenser of claim 1, additionally comprising:

a first hinge flange protruding longitudinally outwardly from said dispenser first end wall, wherein said floss bore door has a door hinged end and a door free end;

and a second hinge flange protruding from said door hinged end and spaced apart sufficiently to receive longitudinally between them said first hinge flange, said first hinge flange and said second hinge flange including registering segments of a hinge pin passageway extending through said first and second door hinge flanges;

and a hinge pin extending through said segments of said hinge pin passageway such that said door pivots on said hinge pin.

7. The dental floss dispenser of claim 6, additionally comprising a door latch notch in said dispenser side wall and a barbed latching tab protruding from said door free end positioned to releasibly and engagingly snap into said door latch notch to releasibly hold said floss bore door closed.

8. The dental floss dispenser of claim 1, additionally comprising an off/on switch controlling the flow of electricity from said battery to said motor.

9. The dental floss dispenser of claim 1, additionally comprising a cluster of fixed bristles extending from said dispenser side wall adjacent to said cluster of movable bristles.

10. The dental floss dispenser of claim 1, wherein said floss bore is wider than said floss spool wound with floss and comprises a plurality of longitudinal guide ribs projecting radially inwardly to loosely abut and slidably retain said floss spool wound with floss, for providing a wider external gripping area and to be light in weight.

* * * * *